(12) United States Patent
Liu et al.

(10) Patent No.: US 11,370,679 B2
(45) Date of Patent: Jun. 28, 2022

(54) METHOD FOR PREDICTING DISCHARGE LEVEL OF EFFLUENT FROM DECENTRALIZED SEWAGE TREATMENT FACILITIES

(71) Applicant: Yangtze Delta Region Institute of Tsinghua University, Zhejiang, Jiaxing (CN)

(72) Inventors: Rui Liu, Jiaxing (CN); Qiangqiang Yu, Jiaxing (CN); Lujun Chen, Jiaxing (CN)

(73) Assignee: YANGTZE DELTA REGION INSTITUTE OF TSINGHUA UNIVERSITY, ZHEJIANG, Jiaxing (CN)

( * ) Notice: Subject to any disclaimer, the term of this patent is extended or adjusted under 35 U.S.C. 154(b) by 78 days.

(21) Appl. No.: 17/001,668

(22) Filed: Aug. 24, 2020

(65) Prior Publication Data
US 2020/0385297 A1    Dec. 10, 2020

Related U.S. Application Data

(63) Continuation-in-part of application No. PCT/CN2019/094668, filed on Jul. 4, 2019.

(30) Foreign Application Priority Data

Jun. 6, 2019 (CN) .......................... 201910492731.5

(51) Int. Cl.
*C02F 3/00* (2006.01)
*G06N 5/04* (2006.01)
(Continued)

(52) U.S. Cl.
CPC ............ *C02F 3/006* (2013.01); *C02F 3/1263* (2013.01); *C02F 3/30* (2013.01); *C02F 3/327* (2013.01);
(Continued)

(58) Field of Classification Search
CPC .... C02F 1/008; C02F 2209/006; C02F 3/006; G01N 33/18; G06N 20/10
(Continued)

(56) References Cited

U.S. PATENT DOCUMENTS 6,656,367 B1 * 12/2003 Audic ....................... C02F 3/00
210/739

FOREIGN PATENT DOCUMENTS

CN            102249411 A   *  11/2011

OTHER PUBLICATIONS

Guoping Sheng, CN10249411 English Machine Translation, pp. 1-8 (Year: 2013).*

* cited by examiner

*Primary Examiner* — Claire A Norris
(74) *Attorney, Agent, or Firm* — Matthias Scholl P.C.; Matthias Scholl

(57) ABSTRACT

A method for predicting a discharge level of an effluent from decentralized sewage treatment facilities, the method including: measuring the conductivity of an influent, the conductivity and suspended solids concentration of an effluent of a plurality of decentralized sewage treatment facilities; repeatedly measuring a pH, a concentration of COD, a concentration of ammonia nitrogen, the concentration of total phosphorus of the effluent of each of the plurality of decentralized sewage treatment facilities; calculating average values of the pH, the concentration of COD, the concentration of ammonia nitrogen, the concentration of total phosphorus; comparing the average values with a local sewage discharge standard, and determining a discharge level of the effluent; constructing a predictive model; and sampling an influent and an effluent of a sewage treatment facility, measuring the conductivity of an influent, the conductivity and suspended (Continued)

solids concentration of the effluent, inputting the obtained data to the predictive model.

5 Claims, 5 Drawing Sheets

(51) Int. Cl.
    *G06N 20/10*     (2019.01)
    *C02F 3/12*     (2006.01)
    *C02F 3/30*     (2006.01)
    *C02F 3/32*     (2006.01)
    *G01N 27/06*     (2006.01)
    *G01N 33/18*     (2006.01)

(52) U.S. Cl.
    CPC .............. *G01N 27/06* (2013.01); *G01N 33/18* (2013.01); *G06N 5/04* (2013.01); *G06N 20/10* (2019.01); *C02F 2209/001* (2013.01); *C02F 2209/05* (2013.01); *C02F 2209/06* (2013.01); *C02F 2209/08* (2013.01); *C02F 2209/10* (2013.01); *C02F 2209/14* (2013.01); *C02F 2209/18* (2013.01)

(58) Field of Classification Search
    USPC ..................................................... 702/19, 25
    See application file for complete search history.

METHOD FOR PREDICTING DISCHARGE LEVEL OF EFFLUENT FROM DECENTRALIZED SEWAGE TREATMENT FACILITIES

CROSS-REFERENCE TO RELATED APPLICATIONS

This application is a continuation-in-part of International Patent Application No. PCT/CN2019/094668 with an international filing date of Jul. 4, 2019, designating the United States, and further claims foreign priority benefits to Chinese Patent Application No. 201910492731.5 filed Jun. 6, 2019. The contents of all of the aforementioned applications, including any intervening amendments thereto, are incorporated herein by reference, inquiries from the public to applicants or assignees concerning this document or the related applications should be directed to: Matthias Scholl P.C., Attn.: Dr. Matthias Scholl Esq., 245 First Street, 18th Floor, Cambridge, Mass. 02142.

BACKGROUND

The disclosure relates to the field of wastewater treatment, and more particularly to a method for predicting a discharge level of an effluent from decentralized sewage treatment facilities.

In rural areas, the sewage treatment facilities are scattered in various places and have relatively small water treatment capacity. The water sampling of the rural sewage treatment facilities is mainly manual, which is time-consuming and laborious. In certain areas, a national standard method is used to monitor the discharge level of the effluent, including but not limited to the detection of a series of parameters of the effluent such as the pH, chemical oxygen demand (COD), ammonia nitrogen ($NH_3$—N), and total phosphorus. The method takes a plenty of time and involves heavy workload, and the measurement results cannot be obtained in real time. Optionally, a spectrum method is also used for sewage detection. However, the detection result is inaccurate.

SUMMARY

The disclosure provides a method for predicting a discharge level of an effluent from decentralized sewage treatment facilities, the method comprising:

1) selecting a plurality of decentralized sewage treatment facilities as a training dataset; measuring a conductivity of an influent, a conductivity and suspended solids concentration of an effluent of each of the sewage treatment facilities; repeatedly measuring a pH, a concentration of COD, a concentration of ammonia nitrogen ($NH_3$—N), a concentration of total phosphorus of the effluent from a discharge outlet of each of the plurality of decentralized sewage treatment facilities; calculating average values of the pH, the concentration of COD, the concentration of ammonia nitrogen, the concentration of total phosphorus; comparing the average values with a local sewage discharge standard, and determining a discharge level of the effluent of each of the plurality of decentralized sewage treatment facilities;

2) inputting the conductivity of the influent, the conductivity and suspended solids concentration of the effluent of each of the plurality of decentralized sewage treatment facilities to a support vector machine, employing the discharge level of the effluent of each of the plurality of decentralized sewage treatment facilities as an output value, to train the training dataset, thereby constructing a predictive model to predict a discharge level of an effluent from a sewage treatment facility sample; and 3) sampling an influent and an effluent of a sewage treatment facility, measuring a conductivity of the influent, a conductivity and suspended solids concentration of the effluent, inputting the conductivity of the influent, the conductivity and the suspended solids concentration of the effluent into the predictive model obtained in 2), thereby obtaining a predictive result of a discharge level of the effluent of the sewage treatment facility.

The sewage can be the domestic wastewater from a septic tank, a kitchen sink and a laundry facility. The main pollutant parameters in the domestic wastewater are COD, total nitrogen, ammonia nitrogen, total phosphorus and suspended solids.

For example, in Alabama of the U. S., the numeric Water Quality Standards for pH and Suspended sediment concentration are 6.5-9.0 (Aquatic and Wildlife) and 25 mg/L (Aquatic and Wildlife cold water), that for Total Ammonia is 24.1 mg/L (Aquatic and Wildlife cold water, pH=7.0). In addition, any source discharging to certain surface water will be required to meet water quality standards for total phosphorus and total nitrogen, such as Verde River and its perennial tributaries from the Verde headwaters to Bartlett Lake, the related Single Sample Maximum criteria are 1 mg/L and 3 mg/L.

Research indicates that the discharge level of the effluent from sewage treatment facilities is related to the conductivity of the influent, the conductivity and the concentration of suspended solids of the effluent. The conductivity of the influent, the conductivity and the concentration of suspended solids of the effluent are input to a support vector machine to construct a predictive model to predict the discharge level of the effluent.

To increase the predictive accuracy of the predictive model, the number of training samples in 1) is greater than 120.

The conductivity of a solution is temperature dependent. In this disclosure, the conductivity at the temperature of 20° C. or 25° C.; is used as a reference value. The conductivity in the disclosure is measured using the identical standard.

The plurality of decentralized sewage treatment facilities is an anaerobic/anoxic/oxic ($A^2O$) treatment system, a constructed wetland system, a sequencing batch reactor (SBR) treatment system, a biological aerated filter (BAF) system, or a combination thereof. The plurality of decentralized sewage treatment facilities each comprises a regulating pool and a sewage treatment device comprising a discharge outlet.

In 1), each of the plurality of decentralized sewage treatment facilities comprises a regulating pool provided with a lifting pump; the conductivity of the influent is measured in the regulating pool after the lifting pump is started for 15 min; synchronously, the conductivity and suspended solids concentration of the effluent are measured in the discharge outlet of each of the plurality of decentralized sewage treatment facilities.

The method to measure the conductivity of the influent, the conductivity and the suspended solids concentration of the effluent comprises: sampling the water from the regulating pool and the discharge outlet to measure the conductivity and the concentration of the suspended solids; or, directly measuring the water in the regulating pool or the discharge outlet with an online conductivity meter or an online suspended solids concentration meter.

The conductivity meter can use an on-line monitoring conductivity meter. The probe of the conductivity meter is fixed on the inner wall of the regulating pool through a bracket, 20-50 cm away from the inner wall of the regulating pool, 0-30 cm below the liquid level, and at the outlet of the return pipe. The probe is protected by a protective sleeve.

Specifically, after 15 min on starting up the lifting pump, the conductivity of the influent, the conductivity and the suspended solids concentration of the effluent are simultaneously measured, and then three or four measurements are performed at intervals of 15 minutes. The average values of the conductivity of the influent, the conductivity and the suspended solids concentration of the effluent are calculated.

Synchronously, the pH, the concentration of COD, the concentration of ammonia nitrogen, and the concentration of total phosphorus are repeatedly measured and the average values thereof are calculated. The average values are compared with a local sewage discharge standard, to reflect a discharge level of the effluent of the sewage treatment facility.

In 1), the discharge level of the effluent includes satisfying the discharge standard or failing to satisfy the discharge standard. The discharge standard can be national standard or a local standard.

Further, in 2), prior to inputting data to the support vector machine, the method comprises inputting the conductivity of the influent, the conductivity and suspended solids concentration of the effluent of each of the plurality of decentralized sewage treatment facilities to a mapminmax function: $y=(x-x_{min})/(x_{max}-x_{min})$, where y refers to a normalized measured data of the conductivity of the influent, and the conductivity and suspended solids concentration of the effluent; x refers to a real-time measured data of the conductivity of the influent, and the conductivity and suspended solids concentration of the effluent; $x_{min}$ is a minimum value of x, and $x_{max}$ is a maximum value of x; when the discharge level of the effluent satisfies the local sewage discharge standard; the discharge level is recorded as 1.

When the discharge level of the effluent fails to satisfy the local sewage discharge standard, the discharge level is recorded as −1.

Further, in 2), the training dataset is trained using Libsvm toolbox; a training comprises optimization of penalty parameter c and radial basis function (RBF) kernel parameter g through grid search algorithm; the optimization comprising modifying the penalty parameter c and kernel parameter g twice with SVMcgForClass function, thereby acquiring an optimal solution to the penalty parameter c and the kernel parameter g.

Further, in 3), the method further comprises preliminarily predicting the discharge level of the effluent of the sewage treatment facility after measuring the conductivity of an influent, the conductivity and suspended solids concentration of the effluent; the preliminary predicting is implemented as follows:

i) When the Suspended Solids Concentration of the Effluent is Greater than a Standard Value, Showing the Discharge Level of the Effluent Fails to Satisfy the Local Sewage Discharge Standard; and ii) when the suspended solids concentration of the effluent is less than or equal to a standard value, inputting the conductivity of the influent, the conductivity and the suspended solids concentration of the effluent into the predictive model obtained in 2).

Advantages of the method for predicting a discharge level of an effluent from a sewage treatment facility according to embodiments of the disclosure are summarized as follows. The method can predict the discharge level of a sewage treatment facility by measuring the conductivity of the influent, the conductivity and suspended solids concentration of the effluent of the sewage treatment facility, compared with conventional measuring methods involving a series of water quality parameters including pH value, concentration of COD and the concentration of ammonia nitrogen, the operation method is real-time, cost-effective, and efficient.

DETAILED DESCRIPTION OF THE EMBODIMENTS

Figure 1:
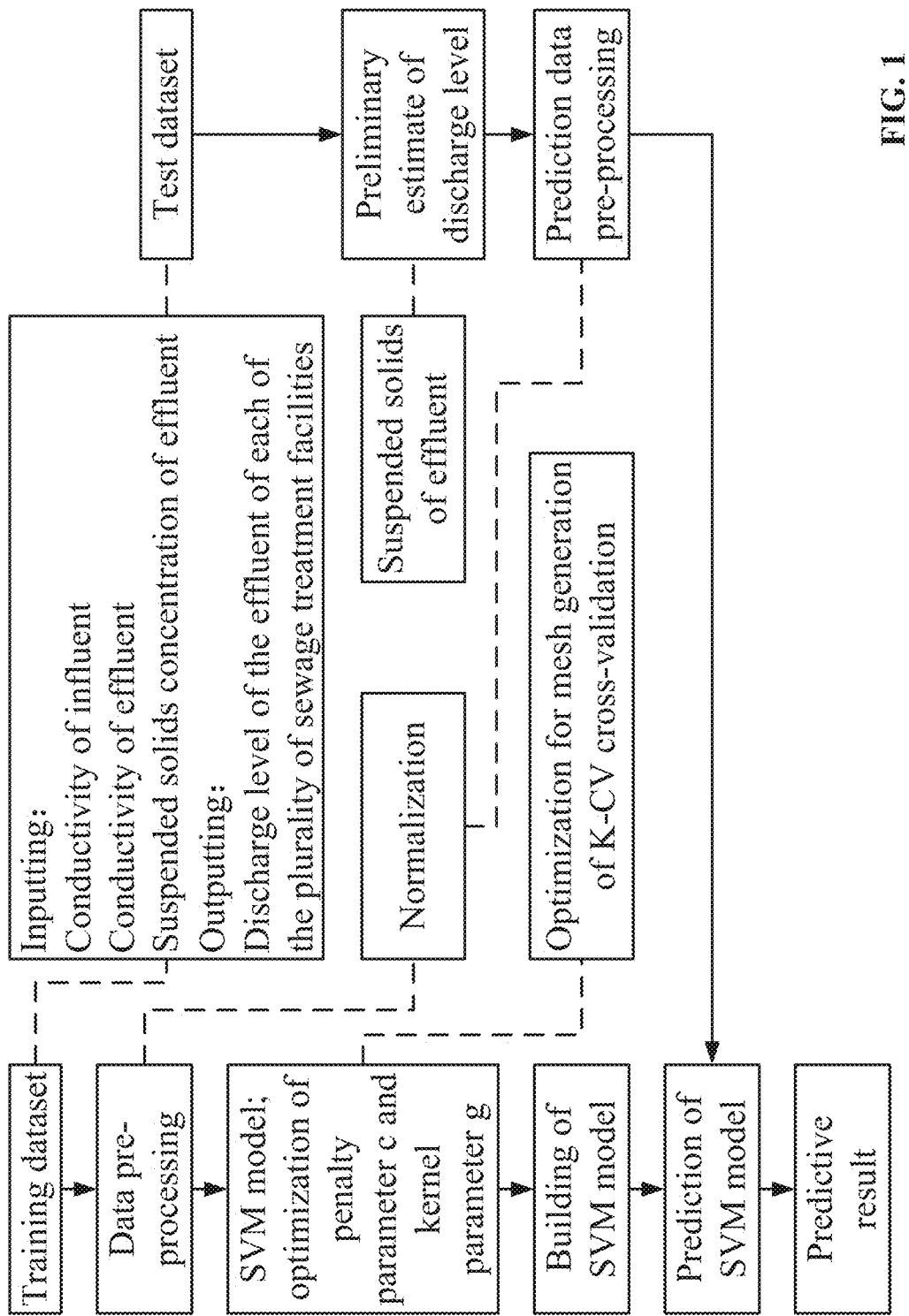
FIG. 1 is a flow chart of a method for predicting a discharge level of an effluent from a sewage treatment facility according to one embodiment of the disclosure.
Figure 2:
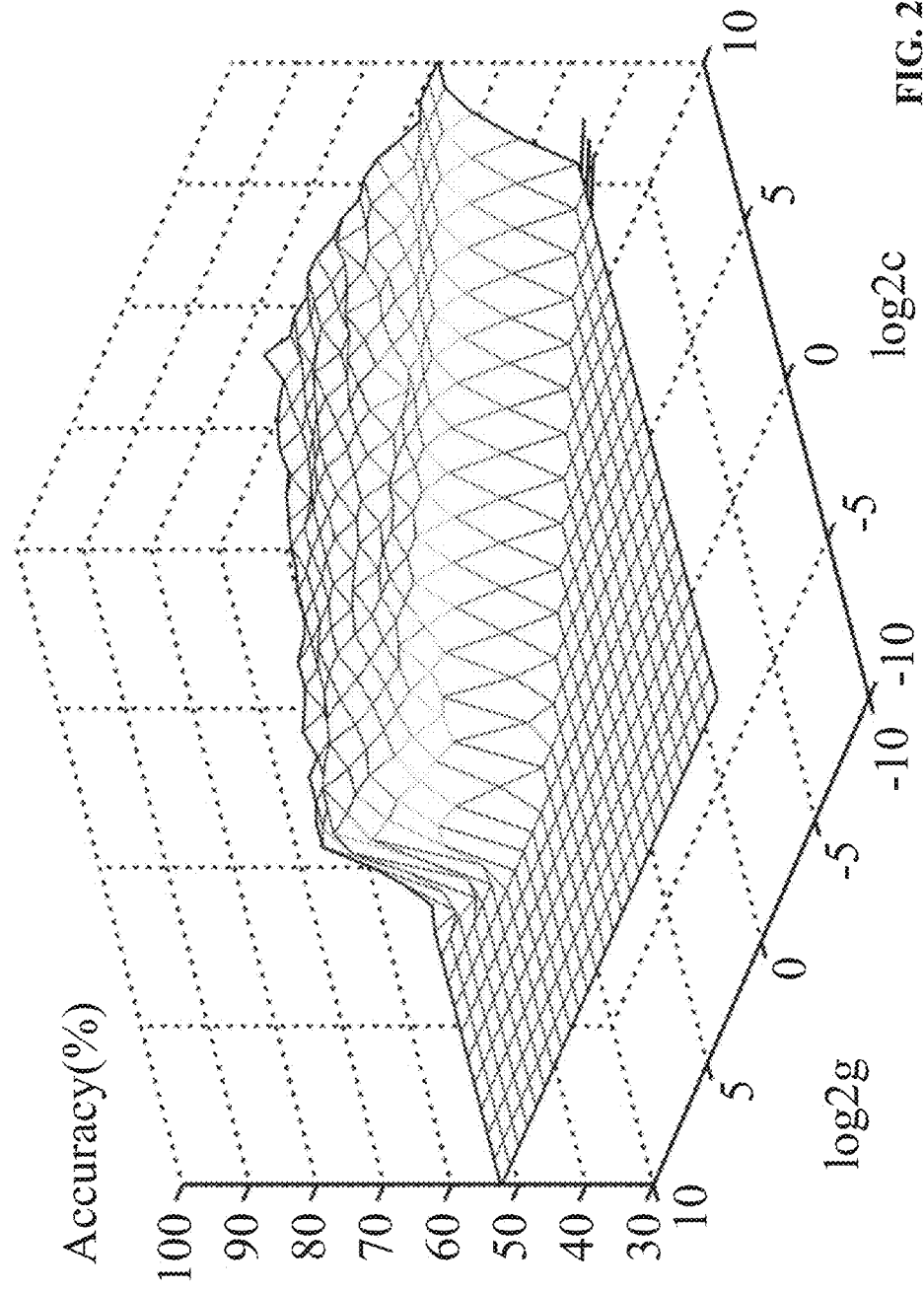
FIG. 2 shows a rough selection result of the optimal penalty parameter c and the optimal kernel parameter g according to one embodiment of the disclosure.
Figure 3:
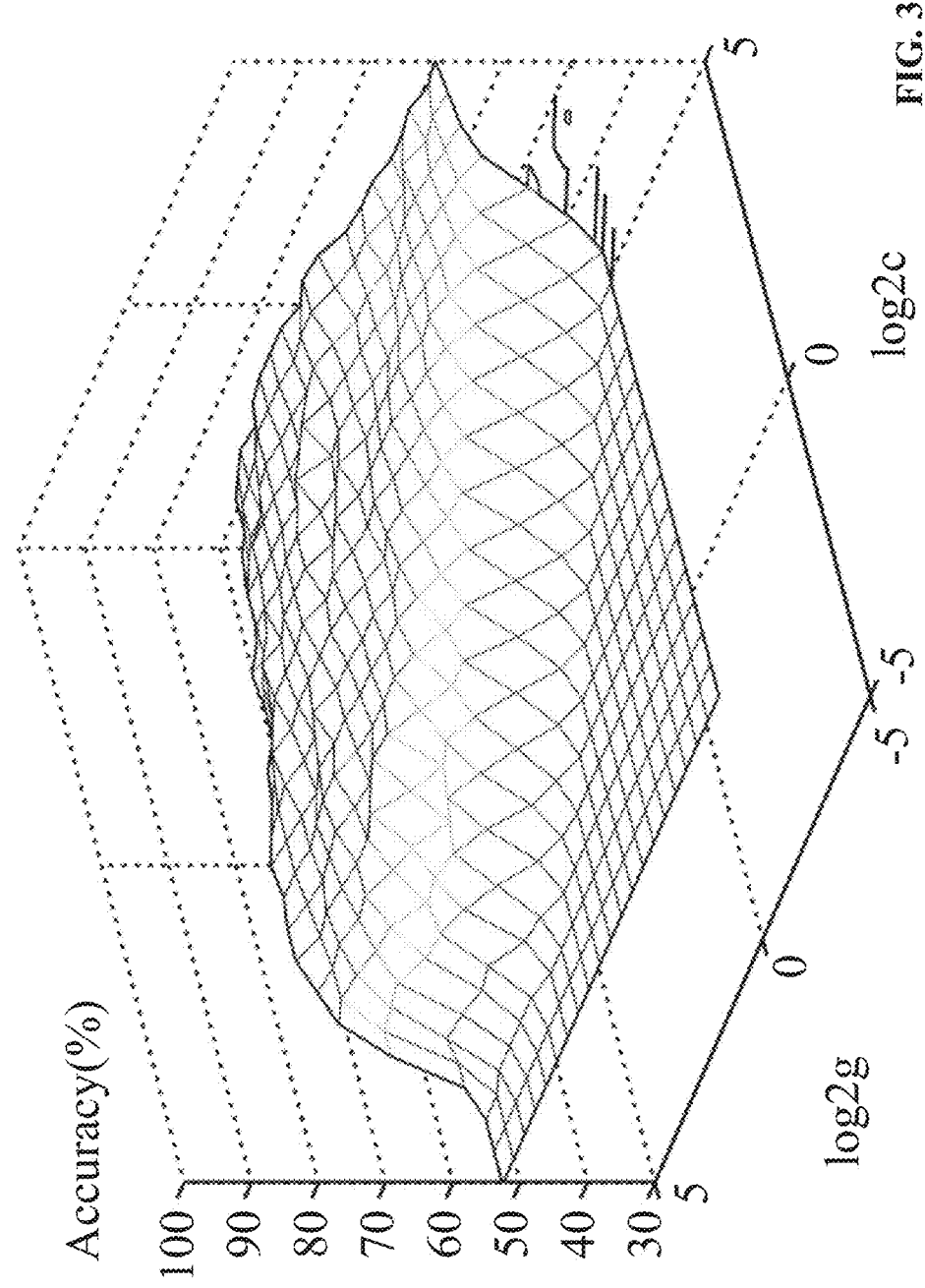
FIG. 3 shows a fine selection result of the optimal penalty parameter c and the optimal kernel parameter g according to one embodiment of the disclosure.
Figure 4:
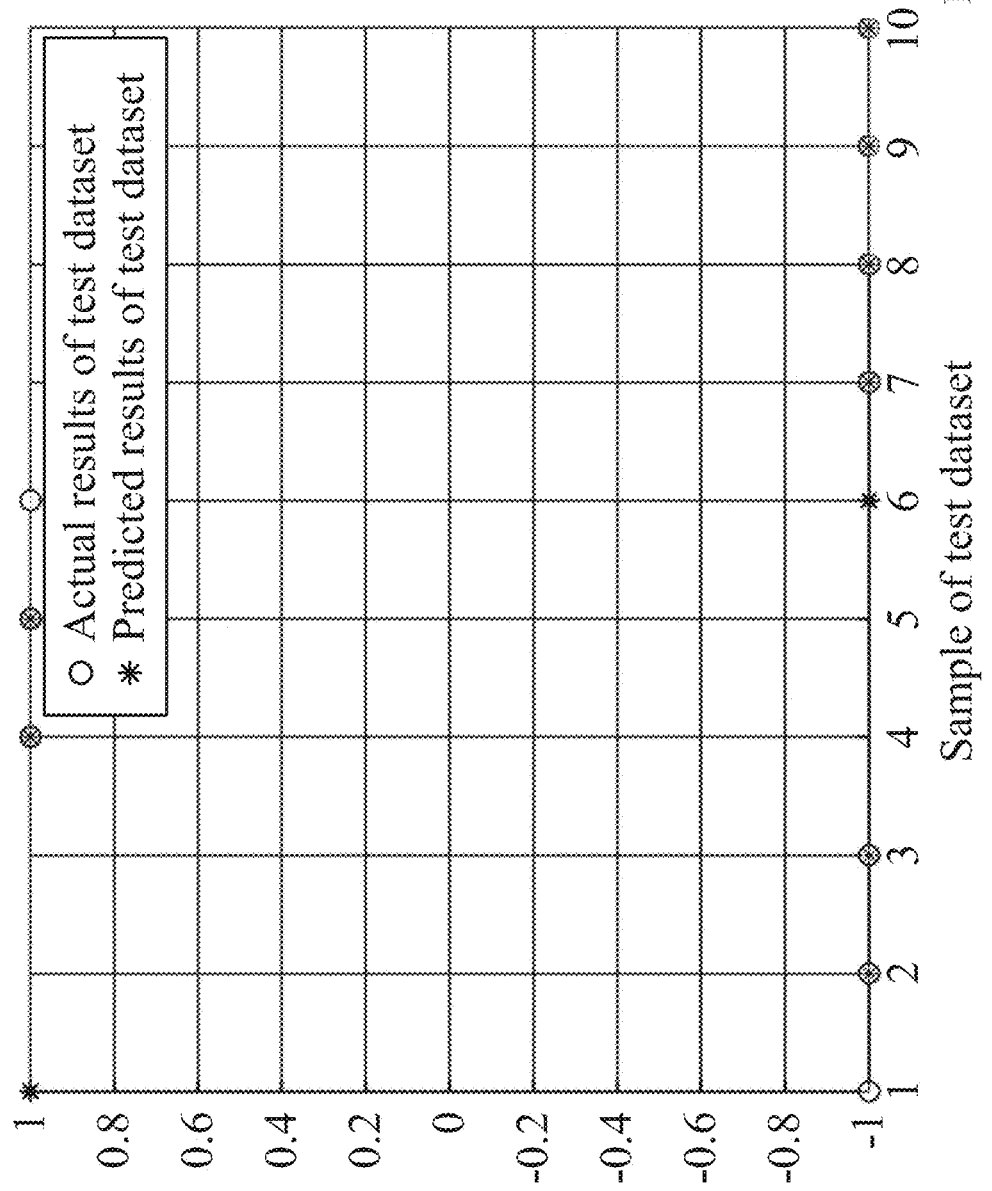
FIG. 4 is a comparison chart of predicted results and actual results according to one embodiment of the disclosure.
Figure 5:
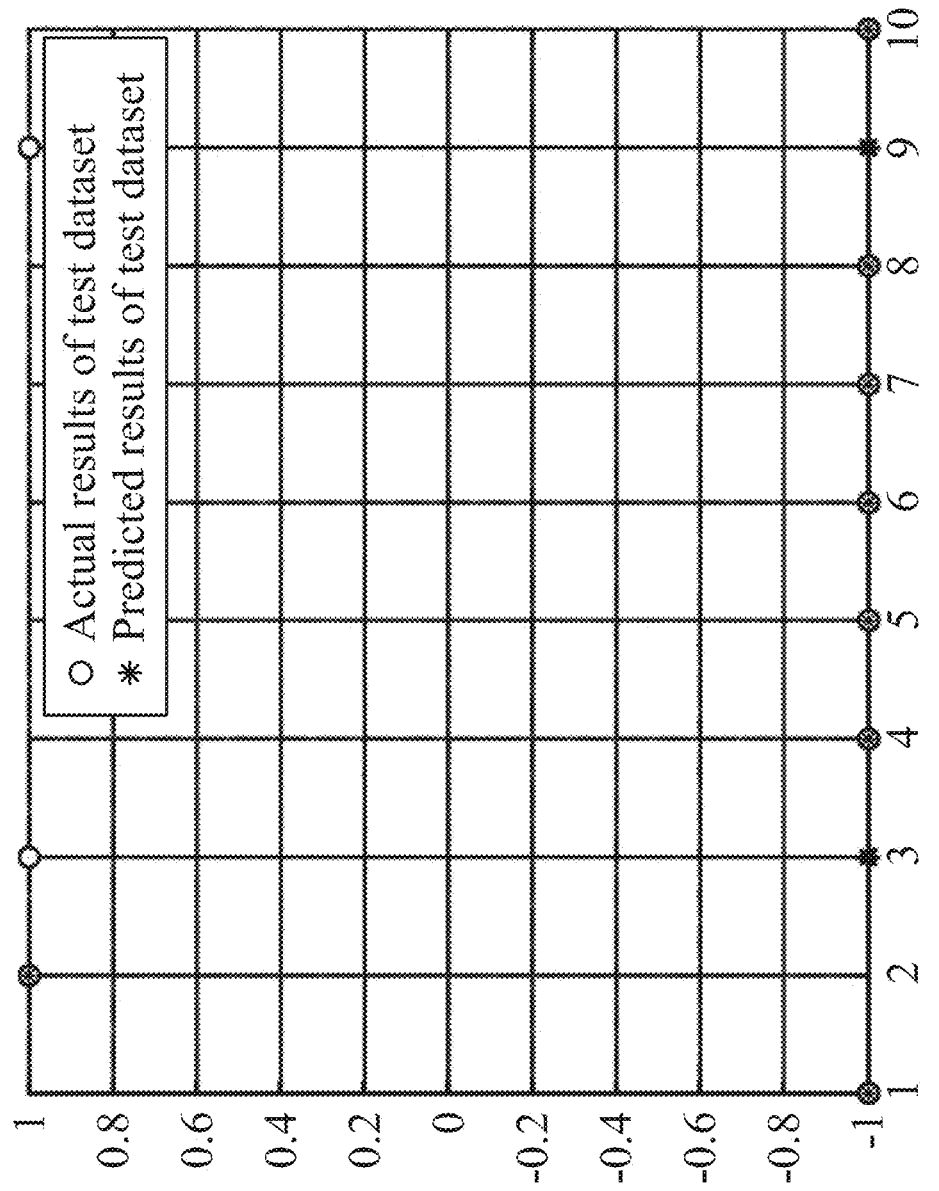
FIG. 5 is a comparison chart of predicted results and actual results according to another embodiment of the disclosure.

To further illustrate the invention, embodiments detailing a method for predicting a discharge level of an effluent from a sewage treatment facility are described below. It should be noted that the following embodiments are intended to describe and not to limit the disclosure.

Example 1

A method for predicting a discharge level of an effluent from a sewage treatment facility is described as follows.

(1) 164 decentralized sewage treatment facilities were selected in rural areas of the Yangtze River Delta, including an anaerobic/anoxic/oxic ($A^2O$) treatment system, a constructed wetland system, a sequencing batch reactor (SBR) treatment system and a biological aerated filter (BAF) system, with a treatment scale of 5-160 t/d. The systems each comprised a regulating pool provided with a lifting pump, and a sewage treatment device provided with a discharge outlet at the water outlet thereof. The rural sewage was from a septic tank, kitchen sinks and laundry facilities. The main water pollutant parameter in the rural sewage were COD, total nitrogen, ammonia nitrogen, total phosphorus and suspended solids.

First, the conductivity of the influent, and the conductivity and suspended solids concentration of the effluent of each of the sewage treatment facilities were measured. Specifically, after 15 min on starting up the lifting pump, the influent from the regulating pool and the effluent from the discharge outlet were sampled and the conductivity of the influent, the conductivity and suspended solids concentration of the effluent were measured. 15 min and 30 min later, the sampling and measurement process were repeated twice.

The average values of the conductivity of the influent, and the conductivity and suspended solids concentration of the effluent were calculated.

Referring to Class II in the standard of "Discharge Standard of Water Pollutants for Sewage treatment Facilities" (DB 33/973-2015) implemented in Zhejiang Province of China, the monitored water quality indicators included pH, COD, ammonia nitrogen, total phosphorus (viewed as phosphorus (P)) and suspended solids (SS), and the corresponding numeric criteria were 6-9, 100 mg/L, 25 mg/L, 3 mg/L, and 30 mg/L, respectively. The concentrations of the water pollutants in the discharge outlet were measured thrice at intervals. The average value of the concentration of each water pollutants were calculated and compared with the local sewage discharge standard, thereby showing the discharge level of the effluent from the sewage treatment facilities. When the discharge level of the effluent satisfied the local sewage discharge level, the discharge level was recorded as 1; when the discharge level of the effluent failed to satisfy the local sewage discharge standard, the discharge level was recorded as −1.

(2). The conductivity of the influent, and the conductivity and suspended solids concentration of the effluent of each of the plurality of decentralized sewage treatment facilities were input to a support vector machine, and the discharge level of the effluent of each of the plurality of decentralized sewage treatment facilities was employed as an output value. 154 sets of data were randomly selected from 164 sets of data as a training dataset, and the training dataset was trained using the support vector machine, thereby constructing a predictive model to predict the discharge level of an effluent from each of the plurality of decentralized sewage treatment facilities.

Specifically, the conductivity of the influent, and the conductivity and suspended solids concentration of the effluent of each of the plurality of decentralized sewage treatment facilities were input to a mapminmax function for normalization, and then input to the support vector machine.

The formula for the mapminmax function was: $y=(x-x_{min})/(x_{max}-x_{min})$ (1), where v referred to a normalized measured data of the conductivity of the influent, and the conductivity and suspended solids concentration of the effluent; x referred to a real-time measured data of the conductivity of the influent, and the conductivity and suspended solids concentration of the effluent; $x_{min}$ was a minimum value of x, and $x_{max}$ was a maximum value of x.

The training was to construct a predictive model to predict the discharge level of the effluent of the sewage treatment facilities using LIBSVM toolbox, and the training comprised optimization of penalty parameter c and Radial Basis Function (RBF) kernel parameter g.

The optimization comprised modifying the penalty parameter c and kernel parameter g twice with SVMcgForClass function, thereby acquiring an optimal solution to the penalty parameter c and the kernel function parameter g.

The first optimization was a rough selection that determined the penalty parameter c within a variation range of $[2^{-10},2^{10}]$ and the kernel parameter g within a variation range of $[2^{-10},2^{10}]$.

(3) The remaining 10 sets of data were employed as a prediction set. The conductivity of the influent, and the conductivity and suspended solids concentration of the effluent of each of the remaining 10 sewage treatment facilities were measured and implemented a preliminary judgment.

A method for the preliminary judgment was to determine whether the effluent satisfied the discharge standard by comparing the suspended solids concentration of the effluent with a standard value stipulated by the local sewage discharge standard.

When the suspended solids concentration of the effluent was greater than the standard value, showing that the discharge level of the effluent failed to satisfy the local sewage discharge standard; when the suspended solids concentration of the effluent was less than or equal to a standard value, the conductivity of the influent, and the conductivity and suspended solids concentration of the effluent were input to the predictive model obtained in 2), thereby obtaining a predictive result of a discharge level of the effluent of the sewage treatment facility.

Predictive results: the actual discharge level determined by the measured values of the effluents of 8 sewage treatment facilities accorded with the predictive result, showing that the prediction was correct. But the predictive result of each of the 2 sewage treatment facilities was different from the measured values, showing that the prediction was wrong. The prediction accuracy was 80%.

Example 2

The effluent samples and the prediction method in this example were the same as that in Example 1, except that the local sewage discharge standard adopted the class I B standard of "Discharge standard of pollutants for municipal wastewater treatment plant".

Predictive results: the actual discharge level determined by the measured values of the effluents of 8 sewage treatment facilities accorded with the predictive result, showing that the prediction was correct. But the predictive result of 2 sewage treatment facilities was different from the measured values, showing that the prediction was wrong. The prediction accuracy was 80%.

It will be obvious to those skilled in the art that changes and modifications may be made, and therefore, the aim in the appended claims is to cover all such changes and modifications.

What is claimed is:

1. A method for treating sewage and discharging treated sewage into the environment, comprising:
 1) proving a first plurality of decentralized sewage treatment facilities, treating sewage using the first plurality of decentralized sewage treatment facilities;
 2) randomly selecting a second plurality of decentralized sewage treatment facilities from the first plurality of decentralized sewage treatment facilities as a training dataset; measuring a conductivity of an influent, a conductivity and suspended solids concentration of an effluent of each of the second plurality of decentralized sewage treatment facilities; repeatedly measuring a pH, a concentration of COD, a concentration of ammonia nitrogen ($NH_3$—N), and a concentration of total phosphorus of the effluent from a discharge outlet of each of the second plurality of decentralized sewage treatment facilities; calculating average values of the pH, the concentration of COD, the concentration of ammonia nitrogen, and the concentration of total phosphorus; comparing the average values of the pH, the concentration of COD, the concentration of ammonia nitrogen, and the concentration of total phosphorus with a local sewage discharge standard, thereby determining a discharge level of the effluent of each of the second plurality of decentralized sewage treatment facilities, wherein the discharge level is a number, and the number is a first preset number when all of the average values of the pH, the concentration of COD, the concentration of ammonia nitrogen, and the concentration of total phosphorus meet the local sewage discharge standard, and the number is a second preset number when one or more of the average values of the pH, the concentration of COD, the concentration of ammonia nitrogen, and the concentration of total phosphorus do not meet the local sewage discharge standard;

3) inputting the conductivity of the influent, the conductivity and suspended solids concentration of the effluent of each of the second plurality of decentralized sewage treatment facilities to a support vector machine, employing the discharge level of the effluent of each of the second plurality of decentralized sewage treatment facilities as an output value, to train the training dataset, thereby constructing a predictive model to predict a discharge level of an effluent from a sewage treatment facility sample; and 4) sampling an influent and an effluent of a sewage treatment facility from the first plurality of decentralized sewage treatment facilities, measuring a conductivity of the influent of the sewage treatment facility, a conductivity and suspended solids concentration of the effluent, inputting the conductivity of the influent, the conductivity and the suspended solids concentration of the effluent into the predictive model obtained in 2), thereby obtaining a predictive result of a discharge level of the effluent of the sewage treatment facility, and discharging the effluent of the sewage treatment facility into the environment when the predictive result of the discharge level of the effluent of the sewage treatment facility is the first preset number.

2. The method of claim 1, wherein the first plurality of decentralized sewage treatment facilities is an anaerobic/anoxic/oxic ($A^2O$) treatment system, a constructed wetland system, a sequencing batch reactor (SBR) treatment system, a biological aerated filter (BAF) system, or a combination thereof.

3. The method of claim 1, wherein in 1), each of the first plurality of decentralized sewage treatment facilities comprises a regulating pool provided with a lifting pump; and measuring the conductivity of the influent, the conductivity and suspended solids concentration of the effluent of each of the second plurality of decentralized sewage treatment facilities comprising: starting the lifting pump; 15 mins later, synchronously measuring the conductivity of the influent in the regulating pool and the conductivity and suspended solids concentration of the effluent in the discharge outlet of each of the second plurality of decentralized sewage treatment facilities.

4. The method of claim 1, wherein in 2), prior to inputting data to the support vector machine, the method comprises inputting the conductivity of the influent, the conductivity and suspended solids concentration of the effluent of each of the second plurality of decentralized sewage treatment facilities to a mapminmax function: $y=(x-x_{min})/(x_{max}-x_{min})$, where y refers to a normalized measured data of the conductivity of the influent, the conductivity of the effluent, or the suspended solids concentration of the effluent; x refers to a real-time measured data of the conductivity of the influent, the conductivity of the effluent, or the suspended solids concentration of the effluent; $x_{min}$ is a minimum value of x, and $x_{max}$ is a maximum value of x; when the discharge level of the effluent satisfies the local sewage discharge standard, the discharge level is recorded as 1; when the discharge level of the effluent fails to satisfy the local sewage discharge standard, the discharge level is recorded as −1.

5. The method of claim 1, wherein in 3), the method further comprises preliminarily predicting the discharge level of the effluent of the sewage treatment facility after measuring the conductivity of an influent, the conductivity and suspended solids concentration of the effluent; the preliminary predicting is implemented as follows:

i) when the suspended solids concentration of the effluent is greater than a standard value, showing the discharge level of the effluent fails to satisfy the local sewage discharge standard; and ii) when the suspended solids concentration of the effluent is less than or equal to a standard value, inputting the conductivity of the influent, the conductivity and the suspended solids concentration of the effluent into the predictive model obtained in 2).

* * * * *